US012514978B2

(12) United States Patent
Riedlinger et al.

(10) Patent No.: US 12,514,978 B2
(45) Date of Patent: Jan. 6, 2026

(54) DEVICE FOR DISPENSING A FLUID DROP-BY-DROP

(71) Applicant: Henke-Sass, Wolf GmbH, Tuttlingen (DE)

(72) Inventors: Axel Riedlinger, Schoemberg (DE); Anika Schmidt, Fridingen (DE); Maikel Wiedmann, Immendingen (DE)

(73) Assignee: Henke-Sass, Wolf GmbH, Tuttlingen (DE)

( * ) Notice: Subject to any disclaimer, the term of this patent is extended or adjusted under 35 U.S.C. 154(b) by 918 days.

(21) Appl. No.: 17/737,014

(22) Filed: May 4, 2022

(65) Prior Publication Data

US 2022/0355028 A1 Nov. 10, 2022

(30) Foreign Application Priority Data

May 5, 2021 (DE) .......................... 102021111630.9

(51) Int. Cl.

*A61M 5/168* (2006.01)
*A61B 5/022* (2006.01)
*A61M 11/06* (2006.01)
*B05B 1/02* (2006.01)

(52) U.S. Cl.

CPC .......... *A61M 5/1689* (2013.01); *A61B 5/022* (2013.01); *A61M 11/06* (2013.01); *B05B 1/02* (2013.01)

(58) Field of Classification Search

CPC . A61M 11/06; B05B 1/02; A61D 7/00; A61D 1/025

See application file for complete search history.

(56) References Cited

U.S. PATENT DOCUMENTS 4,623,337 A 11/1986 Maurice
6,105,828 A 8/2000 Kanner et al.
2005/0261641 A1* 11/2005 Warchol ................ A61F 9/0008 604/294
2009/0223513 A1 9/2009 Papania et al.
2011/0284579 A1* 11/2011 Pardes .................. A61F 9/0008 222/207
2011/0306927 A1* 12/2011 Watanabe ........... A61M 5/5086 604/67
2014/0213989 A1 7/2014 Kelly (Continued)

FOREIGN PATENT DOCUMENTS

WO 2020216673 A2 10/2020

*Primary Examiner* — Bradley J Osinski
(74) *Attorney, Agent, or Firm* — Skaar Ulbrich Macari, P.A.

(57) ABSTRACT

A device for dispensing a fluid drop-by-drop can include a fluid connector to supply the fluid to be dispensed, a pump which is fluidically connected to the fluid connector, an outlet nozzle which is fluidically connected to the pump, an actuating element, and a control unit. When the actuating element is actuated, the control unit activates the pump which pumps the supplied fluid to the outlet nozzle for dispensing drop-by-drop. The outlet nozzle has an outlet opening and a fluid channel which extends as far as the outlet opening and which, in the direction of the fluid from the pump as far as the outlet opening, has a first channel portion with a first cross-sectional surface and a second channel portion with a second cross-sectional surface adjoining the first channel portion. The second cross-sectional surface can be smaller than the first cross-sectional surface.

13 Claims, 4 Drawing Sheets

(56) References Cited

U.S. PATENT DOCUMENTS

| | | | |
|---|---|---|---|
| 2015/0209178 A1 | 7/2015 | Blakey et al. | |
| 2018/0363638 A1* | 12/2018 | Holzhausen ...... | A61M 5/14232 |
| 2021/0197998 A1 | 7/2021 | Lee et al. | |

* cited by examiner

DEVICE FOR DISPENSING A FLUID DROP-BY-DROP

PRIORITY

This application claims the benefit of German Patent Application No. 10 2021 111 630.9, filed on 5 May 2021, which is hereby incorporated herein by reference in its entirety.

FIELD

The present invention relates to a device for dispensing a fluid drop-by-drop.

BACKGROUND

If a fluid to be dispensed is a vaccine, for example, the vaccine may be dispensed drop-by-drop. For example, a dispensing of eye droplets to poultry for vaccination is desirable in order to carry out an ocular vaccination thereby. Hitherto, such an ocular vaccination was carried out by means of a plastics bottle. A droplet is generated at an outlet attachment by manual pressure on the bottle wall. As soon as the droplet has been released, the pressure is withdrawn so that the remaining vaccine is drawn back into the bottle by the prevailing negative pressure. The droplet size and the number of droplets are dependent both on the pressure which is exerted by the user and on the angle at which the bottle is held during the dispensing of the droplets.

In practical use for the ocular vaccination of an animal it may arise that two or more droplets are released, for example, since generally a large number of animals have to be dealt with under significant time pressure. Thus a variance is present according to the user, which, on the one hand, leads to variations in the metering process and, on the other hand, to a vaccine requirement which may be difficult to calculate for a quantitatively defined animal population.

SUMMARY

A device for dispensing a fluid drop-by-drop is provided herein, which remedies the difficulties noted above as comprehensively as possible.

Due to the pump which may be actuated by means of the actuating element, a defined quantity of fluid may always be conveyed to the outlet opening so that the droplet size and the number of droplets may be ensured. The droplet formation is ensured, in particular, by the fluid channel tapering in the direction of the outlet surface since the second cross-sectional surface is smaller than the first cross-sectional surface.

The device may be configured, in particular, such that an actuation of the actuating element, which may be implemented as a push button for example, brings about a defined running time of the pump, so that a defined quantity of fluid is pumped thereby to the outlet opening. A plurality of pump cycles of the pump may be required in order to convey the quantity of fluid for one droplet. If the fluid is a medicine or a vaccine, for example, a droplet size of 0.03 ml may be desired. A plurality of pump cycles (for example four) may be required therefor. The pump may be a diaphragm pump, for example.

The device may have an input module (for example with a display and one or more input elements), the droplet size and/or the number of droplets which are generated when the actuating element is actuated once, for example, being able to be adjusted thereby.

Preferably, the device is configured such that when the actuating element is actuated once, exactly one single droplet is formed and dispensed.

The device may have a counter which counts the total number of droplets dispensed. This number may be shown on the display, for example.

Moreover, the device may have a temperature measuring device for measuring the temperature of the fluid to be conveyed. In this case it may be a temperature sensor which measures, for example, the fluid in the fluid connection to the pump or the fluid in the fluid connection from the pump as far as the fluid connector (preferably at a defined point). The measured temperature may be displayed, for example, on the display in order to inform the user, and/or may be used for outputting a warning when a definable threshold value is exceeded or fallen below or when the measured temperature is outside a definable interval.

The measured temperature may be supplied to a control unit of the device for dispensing a fluid drop-by-drop, said control unit adapting the motor running time, when the actuating element is actuated, as a function of the temperature, for example, in order to ensure that the same quantity of fluid is conveyed or pumped. Thus, for example, the viscosity of the fluid may increase with a rising temperature, which leads to a longer pump running time in order to convey the same quantity of fluid.

The measured temperature may also be used in a calibration mode of the device for adapting the pump running time.

Moreover, the fluid channel may have a third channel portion adjoining the second channel portion, said third channel portion extending as far as the outlet opening and having a third cross-sectional surface which is larger than the second cross-sectional surface. This promotes the droplet formation. Moreover, the third channel portion may be configured, in particular, to be cylindrical, wherein the diameter thereof is adapted to the desired droplet size.

Thus the outlet nozzle may have a replaceable end cap with the third channel portion so that different end caps with different diameters or cross-sectional surfaces of the third channel portion may be provided, in each case the end cap which has the desired diameter (or the desired cross-sectional surface) of the third channel portion for the required droplet size being selected therefrom.

The outlet nozzle may have at the outlet opening a first region with a first external diameter and a second region with a second external diameter adjoining thereto in the direction counter to the direction of the fluid, wherein the second external diameter is smaller than the first external diameter. The first region preferably terminates at the distal end of the outlet nozzle. Thus an external groove is present, which is advantageous for the desired droplet break-off at the outlet opening.

Moreover, the inner edge of the outlet opening may be configured to be sharp-edged. Furthermore, the external edge may be configured to be sharp-edged at the outlet opening. "Sharp-edged" is understood to mean here, in particular, that a beveled edge is not formed and/or that the material boundary surfaces abutting the respective edge enclose an angle ranging from 80° to 100°, and preferably ranging from 85° to 95° and, in particular, preferably an angle of 90°.

For a droplet of 0.03 ml the third channel portion (which preferably comprises a circular cross section) has a diameter of 1.5 mm, for example. The diameter may range from 0.5 mm to 3 mm (preferably to 2 mm). The cross-sectional surface of the third channel portion may range from 0.20 to 7.07 $mm^2$. When the droplet size increases, the optimal diameter of the third channel portion increases.

The first channel portion (which preferably comprises a circular cross section) can comprise a diameter from 3 to 6 mm, for example. The cross-sectional surface of the first channel portion may range from 7.07 to 28.27 $mm^2$.

The second channel portion can comprise one, two or more second sub-sections, which comprise a circle segment shaped cross section, for example. The cross-sectional surface of the second channel portion may range from 0.05 to 1 $mm^2$, preferably from 0.1 to 0.5 $mm^2$, and in particular preferably from 0.15 to 0.30 $mm^2$.

In particular, the third cross-sectional surface can be smaller than the first cross-sectional surface.

Preferably, the second channel portion directly adjoins the first channel portion. Further, the second channel portion can directly adjoin the first channel portion.

In particular, droplets having a volume of 0.025 ml to 0.04 ml may be generated by the device.

For example, 10, 20, 30, 40, 50, 60, 70, 80, 90 or 100 droplets may be generated per minute. When generating exactly one droplet per actuation of the actuating element, this number is substantially limited by how rapidly the actuating element is able to be repeatedly actuated.

It has been shown that an improved droplet formation may be achieved if the fluid channel of the outlet nozzle is configured such that a linear through-flow is prevented.

Moreover, it is advantageous if a non-return valve is arranged in the fluid channel of the outlet nozzle, said non-return valve opening from a predetermined pressure of the fluid coming from the pump and thus producing a fluidic connection of the pump with the outlet opening. As a result, a deceleration of the speed of the pumped fluid may be produced, which in turn contributes to the droplet formation and, in particular, prevents the fluid from being dispensed as a stream. This non-return valve thus primarily serves to ensure the droplet formation.

Moreover, the device may have an inclination sensor which measures the current inclination of the device and thus of the outlet nozzle relative to the surface of the earth and delivers this measurement to the control unit. The device may be designed such that an actuation of the actuating element only activates the pump when the measured inclination is within a predetermined inclination range. In this case, for example, it may be the inclination range of 30° to 40°. If a user holds the device at this inclination, by actuating the actuating element the desired number of droplets may be dispensed. The device may be configured such that it communicates to the user acoustically, haptically and/or optically that the user is holding the device such that the inclination is, or is not, within the predetermined inclination range.

For adjusting the volume, the control unit may detect from which point a motor of the pump starts to rotate, after the pump has been activated by actuating the actuating element. This point in time is not the same with each actuation of the actuating element but depends on external influence factors, such as for example the resistance which the motor has to encounter in order to start up. From this time the pump is supplied with voltage for a defined time period, and at the end of the time period the motor of the pump is actively braked. As a result, it is achieved that the indefinable influences of the motor start-up time and motor braking time are minimized. An active braking may be achieved, for example, by the operating direction of the motor being reversed at the end of the time period, so that the motor attempts to rotate the motor shaft in the opposing direction.

The device is preferably calibrated. In this case, the user may carry out the calibration by simple means. To this end, the user may select a calibration mode via the input unit, wherein a specific target volume is predetermined, for example for a specific medicine. Alternatively, the user may select or predetermine a target volume. As soon as this is completed, the user actuates the actuating element sufficiently often until the user has dispensed the defined target volume into a vessel. The control unit of the device determines the optimal active pump running time from the number of actuations required to reach the target volume. By this type of calibration it is possible to compensate for external influences on the conveying behavior of the pump. In this case, for example, these external influences may be the type of fluid, the temperature of the fluid and the pretensioning of the non-return valve in the fluid channel of the outlet nozzle. Specifically, the pretensioning of the non-return valve varies, primarily due to unavoidable production tolerances.

The fluid to be dispensed may be, in particular, a liquid. Preferably the fluid may be a medicine, an active ingredient or a vaccine. The dispensing drop-by-drop by means of the device may be used for dispensing into an eye, a body orifice or onto the skin of an animal (for example of poultry).

A reservoir of the fluid may be connected to the fluid connector. In this case, for example, the reservoir may be a container having the fluid, such as for example a medicine bottle. However, a tube connection to a fixed reservoir is also possible.

The device can be configured as a portable appliance. The device may have a housing with a grip portion which preferably may be held by one hand. The actuating element may be provided on the grip portion. In particular, it may be provided that a user may operate the actuating element with the index finger of the hand holding the grip portion.

A method for dispensing a fluid drop-by-drop is also provided, wherein a device is used with a fluid connector, the fluid to be dispensed being able to be supplied thereby, a pump which is fluidically connected to the fluid connector, an outlet nozzle which is fluidically connected to the pump and an actuating element which, when actuated, activates the pump which pumps the supplied fluid to the outlet nozzle for dispensing drop-by-drop, wherein the outlet nozzle has an outlet opening and a fluid channel which extends as far as the outlet opening and which, in the direction of the fluid in the pump as far as the outlet opening, has a first channel portion with a first cross-sectional surface and a second channel portion with a second cross-sectional surface adjoining the first channel portion, wherein the second cross-sectional surface is smaller than the first cross-sectional surface, wherein the actuating element is actuated for dispensing a droplet.

The method may also be developed in the same manner as the device.

It goes without saying that the features which are mentioned above and which are to be described in more detail below are able to be used not only in the specified combinations but also in other combinations or individually without departing from the scope of the present invention.

The invention is described below in more detail by means of exemplary embodiments with reference to the accompanying drawings, which also disclose features essential to the invention. These exemplary embodiments merely serve for illustration and are not to be interpreted as limiting. For example, a description of an exemplary embodiment with a plurality of elements or components is not to be interpreted such that all of these elements or components are required for the implementation. Rather, other exemplary embodiments may also contain alternative elements and components, fewer elements or components, or additional elements or components. Elements or components of different exemplary embodiments may be combined together unless specified otherwise. Modifications and changes which are described for one of the exemplary embodiments may also be applicable to other exemplary embodiments. To avoid repetition, elements which are the same or correspond to one another are denoted in the different figures by the same reference numerals and are not repeatedly described.

DETAILED DESCRIPTION

Figure 1:
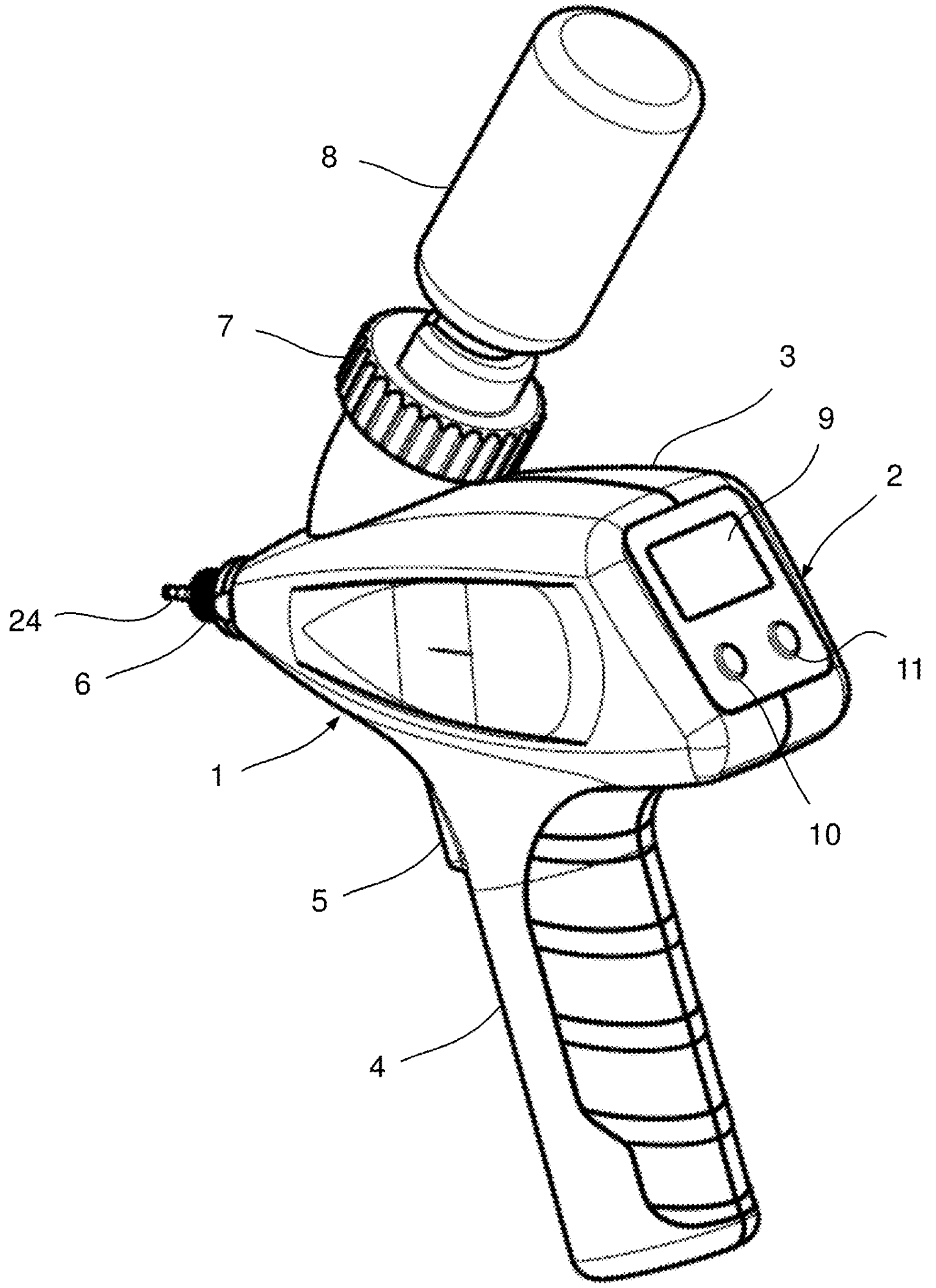
FIG. 1 shows an isometric view of an exemplary embodiment of the device for dispensing according to certain embodiments.

In the exemplary embodiment shown in FIG. 1, for dispensing a fluid into an eye drop-by-drop, the device 1 according to the invention comprises a housing 2 with a main portion 3 and a grip portion 4. The grip portion 4 is configured such that a user may hold the device 1 by gripping around the grip portion 4 with one hand. Moreover, the grip portion 4 has a start button 5 for actuating the device 1. A dispensing region 6 is configured on the front end of the main portion 3. Moreover, on the upper region of the main portion 3 the device 1 has a connector 7, in the embodiment shown in FIG. 1 a container 8 with a fluid to be dispensed (in this case in the form of a medicine bottle) being fastened thereto.

A display 9 and two operating elements 10, 11 are provided at the rear end of the main portion 3.

Figure 2:
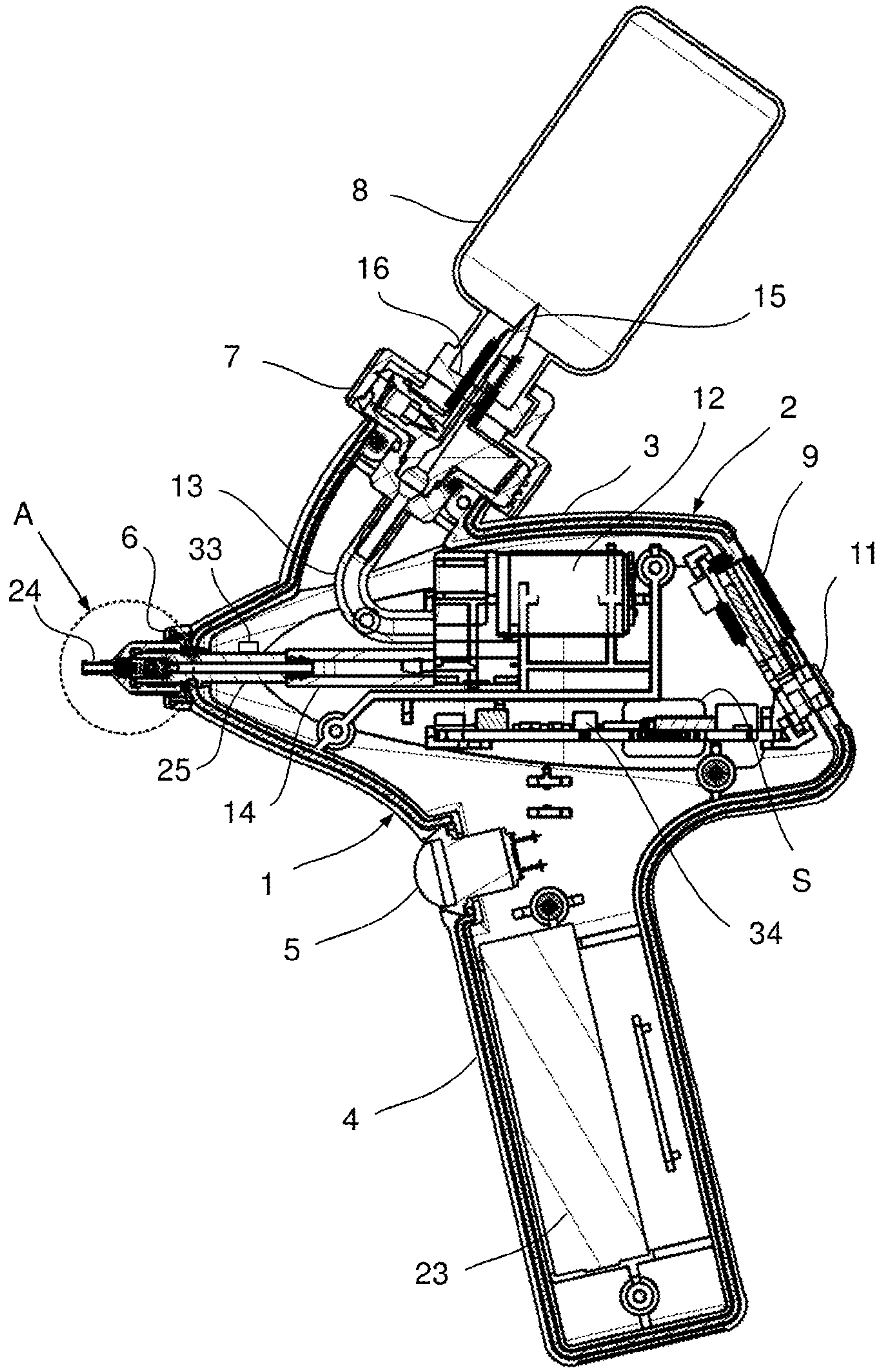
FIG. 2 shows a sectional view of the device 1 of FIG. 1.

As is visible most clearly in the sectional view in FIG. 2, a pump 12 which is connected via a first fluid connection 13 to the connector 7 and via a second fluid connection 14 to the dispensing region 6 is provided in the main portion 3. In this case, tubes are used for the two fluid connections 12 and 14.

The connector 7 has a piercing needle 15 by which a diaphragm 16 on the container 8 is pierced when the container 8 is attached, in order to ensure in this manner a connection of the fluid from the interior of the container 8 to the first fluid connection 13. The piercing needle 15 further comprises a valve which ensures an automatic ventilation of the container 8 and thus the required pressure compensation.

The pump 12 may be, for example, a diaphragm pump 12 which is designed for micro flow rates since the droplets to be dispensed are intended to have a volume of ca. 0.03 ml, for example.

The underlying principle of such a diaphragm pump 12 is described in more detail with reference to the schematic view of FIGS. 3 and 4. The pump 12 comprises a pump chamber 17 with a pump inlet 18 and a pump outlet 19 which in each case are closed by a non-return valve 20, 21. The non-return valves 20, 21 are arranged such that a flow of the fluid to be pumped is possible only from the pump inlet 18 into the pump chamber 17 and therefrom to the pump outlet 19. The pump chamber 17 is defined on one side by a diaphragm 22 which is formed, for example, from a flexible elastomer. The diaphragm 22 may be set in vibration by the pump 12 by means of a motor (not shown) via an eccentric (not shown), such that by a movement of the diaphragm 22 upwardly (arrow P1 in FIG. 3) the volume of the pump chamber 17 is increased and by a movement of the diaphragm 22 downwardly (arrow P2 in FIG. 4) the volume of the pump chamber 17 is reduced.

Figure 3:
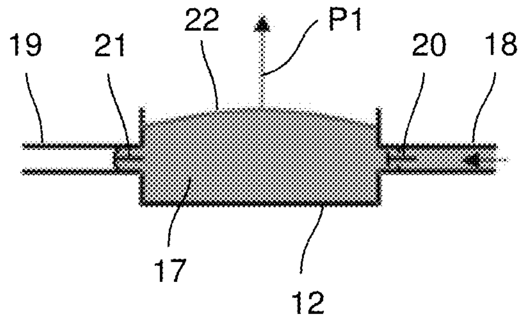
FIGS. 3 and 4 show schematic views for describing the mode of operation of a diaphragm pump.
Figure 4:
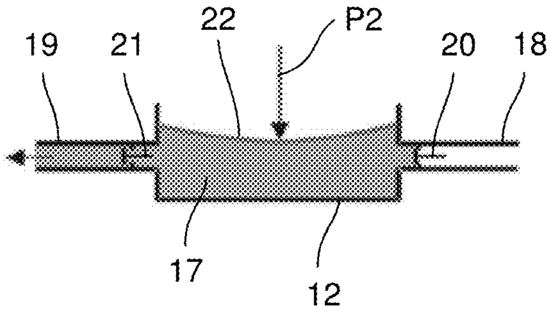

When increasing the volume of the pump chamber 17 according to FIG. 3 a negative pressure is generated in the pump chamber 17, whereby fluid is suctioned into the pump chamber 17 via the pump inlet 18. When the volume of the pump chamber 17 is reduced (FIG. 4) an overpressure is generated, whereby fluid is forced out of the pump chamber 17 to the pump outlet 19.

Moreover, a control unit S (FIG. 2) which, for example, has a processor and a memory is provided. The control unit S serves for controlling the pump 12, is connected to the start button 5 and the operating elements 10, 11 and generates the data and information which are shown on the display 9.

Since in the device 1 according to the invention the first fluid connection 13 is connected to the pump inlet 18 and the second fluid connection 14 is connected to the pump outlet 19, by actuating the pump 12 fluid may be transported from the container 8 to the dispensing region 6.

The activation of the pump 12 is carried out via the actuation of the start button 5, wherein after the start button 5 has been actuated a predetermined number of pump cycles is carried out, due to the control by means of the control unit S, in order to convey the volume required for at least one droplet to be dispensed. An energy source 23 or a power supply 23 (in this case for example a rechargeable battery or a battery) is provided in the grip portion 4 for supplying energy to the pump 12 and the control unit S.

Figure 5:
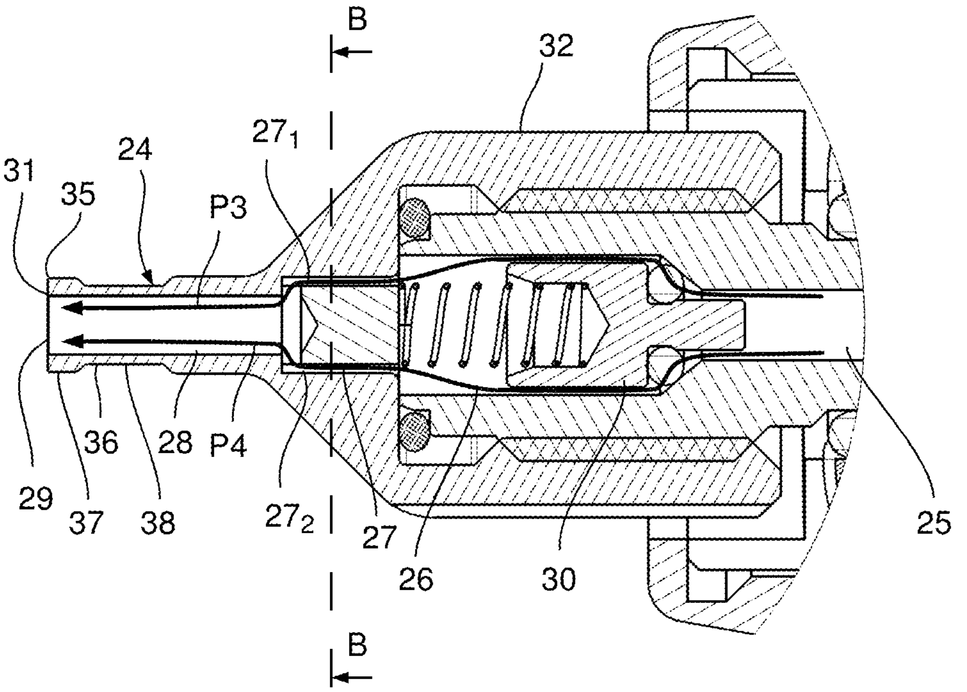
FIG. 5 shows an enlarged sectional view of the detail A of FIG. 2.

In order to prevent the volume of fluid conveyed by the pump 12 from being dispensed as a stream at the dispensing region 6 of the device 1, the outlet nozzle 24 shown in the enlarged sectional view in FIG. 5 is provided in the dispensing region 6. The outlet nozzle 24 has an inlet portion 25, which is connected to the second fluid connection 14, a first, second and third channel portion 26, 27, and 28, an outlet opening 29, as well as a non-return valve 30.

In the position shown in FIG. 5 of the non-return valve 30, this non-return valve closes the inlet portion 25.

From the application of a predetermined pressure (in this case for example 250 mbar) of the fluid conveyed by the pump 12, the non-return valve 30 is moved toward the outlet opening 29 so that it opens and the fluid may flow through the channel portions 26 to 28, as indicated by the arrows P3 and P4.

Figure 6:
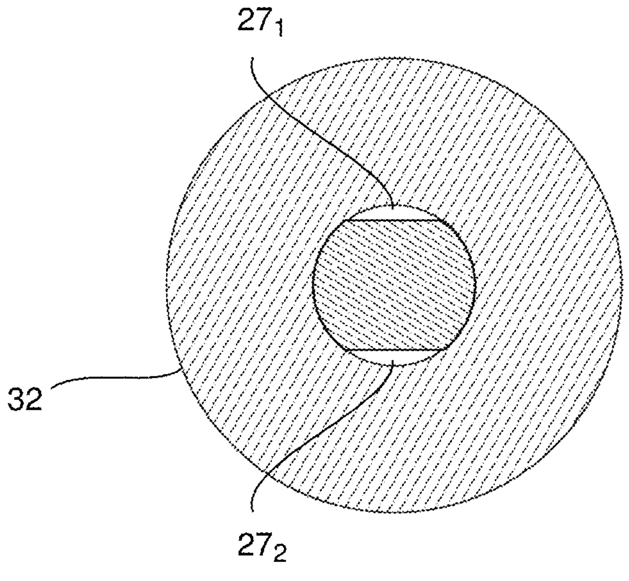
FIG. 6 shows a sectional view along the section line B-B in FIG. 5.

As may be further derived from the sectional view of the outlet nozzle 24 in FIG. 5 as well from the sectional view of FIG. 6, the cross-sectional surface of the second channel portion 27 is smaller than the cross-sectional surface of the first channel portion 26. The second channel portion 27 is formed by two channel sub-portions $\mathbf{27_1}$ and $\mathbf{27_2}$, each of which comprises a circle segment shaped cross section. The second channel portion 27 has a cross-sectional surface of 0.17 $mm^2$ according to the present embodiment, whereas the cross section of the first channel section 26 is circular having a surface of 10.18 $mm^2$. Moreover, the cross-sectional surface of the second channel portion 27 is also smaller than the cross-sectional surface of the third channel portion 28, wherein the cross section of the third channel section 28 is circular having a surface of 1.77 $mm^2$. By this reduction in the cross-sectional surface, in combination with the non-return valve 30, a deceleration of the fluid flow which is generated by the pump 12 is achieved, whereby the fluid is dispensed in droplet form via the outlet opening 29 (not as a fluid stream). Thus, for example, the dispensing of the fluid into an eye (for example an animal eye) may be carried out drop-by-drop. Such a dispensing drop-by-drop may be used, for example, for vaccinating animals and thus for ocular vaccination. In this manner, for example, an ocular vaccination may be carried out on poultry. The device 1 according to the invention thus may also be denoted as an electronic hand-held appliance 1 for ocular vaccination.

Moreover, the outlet opening 29 has an edge shape of the inner edge 31 which is advantageous for the desired droplet break-off and thereby prevents the droplet from remaining suspended on the outlet nozzle 24. In particular, the edge shape of the inner edge 31 is selected such that it is as sharp-edged as possible and, for example, a beveled edge is not provided at the distal end of the outlet opening 29. This sharp-edged characteristic of the outlet opening 29 promotes the droplet break-off since, as a result, the surface area is minimized and the fluid (or the liquid) adheres less easily to the outlet nozzle. In addition to the sharp-edged configuration of the inner edge 31 (the internal edge) of the outlet opening 29, the outer edge 35 at the distal end may also be configured to be sharp-edged (for example without a beveled edge). This also promotes the droplet break-off. "Sharp-edged" is understood to mean here that the material boundary surfaces abutting the respective edge enclose an angle ranging from 80° to 100° and preferably ranging from 85° to 95° and particularly preferably of 90°. Moreover, the outer edge 35 is preferably configured without a beveled edge.

Additionally, an outer groove 36 (reduction in the external diameter at the distal end in the region of the third channel portion 28) is provided, said outer groove preventing the fluid or the liquid from running along the outlet nozzle 24, which would lead to an undesired increase in the contact surface area. The outer groove 36 is also advantageous for the desired droplet break-off. By means of the groove 36, the outlet nozzle 24 has at the outlet opening 29 a first region 37 with a first diameter and a second region 38 with a second external diameter adjoining the first region 37 in the direction counter to the direction of the fluid, wherein the second external diameter is smaller than the first external diameter.

As shown in FIG. 5 the outlet nozzle 24 may have a replaceable end cap 32 which comprises the third channel portion 28. To this end, the end cap 32 may be configured, for example, to be screwable.

Since the internal diameter or the cross-sectional surface of the third channel portion 28 influences the droplet size, a plurality of end caps 32 with different third channel portions 28 which differ in the cross-sectional surface thereof or in the internal diameter may be provided. By selecting the respectively suitable end cap 32, therefore, the desired droplet size may be adjusted thereby.

Moreover, the device 1 may have a temperature sensor 33 (see FIG. 2) which measures the temperature of the fluid immediately upstream of the outlet nozzle 24. The measurement signal or the measurement variable is communicated to the control unit S, since the temperature sensor 33 is connected to the control unit S. Depending on the measured temperature, therefore, the control unit S may carry out changes in the activation of the pump 12 after the start button 5 has been actuated, if this is required. Thus, for example, the viscosity of medicines and vaccines changes with the temperature, which may be compensated, for example, by longer or shorter pumping times so as always to generate the same droplet size. It may also be necessary that a dispensing drop-by-drop is desired only beyond a certain temperature of the fluid. In this case, for example, a dispensing may be prevented below the predetermined temperature by the control unit S and/or the measured fluid temperature may be shown on the display 9.

Moreover, the device 1 may have an inclination sensor 34 (FIG. 2) which is also connected to the control unit S. The inclination sensor 34 measures the inclination of the device and thus of the outlet nozzle 24 relative to the surface of the earth. The control unit S may be designed such that an activation of the pump 12 takes place after the start button 5 has been actuated only when the inclination of the device 1 measured at this moment in time has a predetermined value or is within a predetermined range. Thus, for example, it may be the case that the device 1 is designed for dispensing drop-by-drop at an inclination of 35°. In this case, the control unit may be designed, for example, such that dispensing is only possible when the measured inclination deviates by no more than ±1°, ±2°, ±3°, ±4°, ±5° or ±6° from the predetermined inclination (in this case 35°). This also serves to ensure a reproducible droplet size.

The device 1 may be designed such that it is communicated to the user acoustically, haptically and/or optically whether the inclination of the device 1 is within the permitted range or outside the permitted range.

What is claimed is:

1. A device for dispensing a fluid drop-by-drop, comprising:

a fluid connector that supplies the fluid to be dispensed;
a pump fluidically connected to the fluid connector;
an outlet nozzle fluidically connected to the pump;
an actuator; and
a control unit that activates the pump when the actuator is actuated, wherein the pump pumps the supplied fluid to the outlet nozzle for dispensing drop-by-drop,
wherein the outlet nozzle includes an outlet opening and a fluid channel which extends as far as the outlet opening and which, in the direction of the fluid from the pump as far as the outlet opening, includes a first channel portion with a first cross-sectional surface and a second channel portion with a second cross-sectional surface adjoining the first channel portion,
wherein the second cross-sectional surface is smaller than the first cross-sectional surface, and
wherein the pump comprises a motor operatively coupled to the control unit,
wherein, when the pump is activated, the control unit detects when the motor of the pump starts to rotate, and from this time, after the defined time period for the operation of the pump has elapsed, actively brakes the motor of the pump.

2. The device of claim 1, wherein the fluid channel includes a third channel portion adjoining the second channel portion, said third channel portion extending as far as the outlet opening and having a third cross-sectional surface which is larger than the second cross-sectional surface.

3. The device of claim 2, wherein the third channel portion extends in a linear manner.

4. The device of claim 2, wherein the outlet nozzle includes a replaceable end cap in which the third channel portion is configured.

5. The device of claim 2, wherein the outlet nozzle includes at the outlet opening a first region with a first external diameter, wherein a second region with a second diameter adjoins the first region in the direction counter to the direction of the fluid, wherein the second diameter is smaller than the first diameter.

6. The device of claim 2, wherein the third cross-sectional surface of the third channel portion is smaller than the first cross-sectional surface of the first channel portion.

7. The device of claim 1, wherein an inner edge of the outlet opening is sharp-edged.

8. The device of claim 1, wherein the fluid channel of the outlet nozzle is configured such that a linear through-flow is prevented.

9. The device of claim 1, wherein a non-return valve is arranged in the fluid channel of the outlet nozzle, said non-return valve opening from a predetermined pressure of the fluid coming from the pump and thus producing a fluidic connection of the pump with the outlet opening.

10. The device of claim 1, wherein the pump is a diaphragm pump.

11. The device of claim 1, wherein a plurality of pump cycles of the pump are required in order to convey the volume of fluid for one droplet to be dispensed.

12. The device of claim 1, further comprising a temperature measuring device that measures the temperature of the fluid to be dispensed and forwards the measured temperature to the control unit, wherein the control unit varies the activation of the pump as a function of the measured temperature in order to compensate for a temperature-induced volume change of the conveyed volume.

13. The device of claim 1, further comprising an inclination sensor that measures the inclination of the device relative to a surface of the earth and forwards the inclination measurement to the control unit, wherein the control unit only activates the pump after the actuator is actuated, when the measured inclination is within a predetermined inclination range.

* * * * *